(12) United States Patent
Lebreton

(10) Patent No.: US 9,062,130 B2
(45) Date of Patent: *Jun. 23, 2015

(54) CROSS-LINKING OF LOW-MOLECULAR WEIGHT AND HIGH-MOLECULAR WEIGHT POLYSACCHARIDES, PREPARATION OF INJECTABLE MONOPHASE HYDROGELS, POLYSACCHARIDES AND HYDROGELS OBTAINED

(71) Applicant: Allergan Industrie SAS, Pringy (FR)

(72) Inventor: Pierre F. Lebreton, Annecy (FR)

(73) Assignee: Allergan Industrie SAS, Pringy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/024,916

(22) Filed: Sep. 12, 2013

(65) Prior Publication Data

US 2014/0011990 A1 Jan. 9, 2014

Related U.S. Application Data

(60) Continuation of application No. 13/566,767, filed on Aug. 3, 2012, now Pat. No. 8,563,532, which is a continuation of application No. 12/782,488, filed on May 18, 2010, now Pat. No. 8,338,388, which is a division of application No. 10/552,309, filed as application No. PCT/FR2004/000870 on Apr. 8, 2004, now Pat. No. 7,741,476.

(30) Foreign Application Priority Data

Apr. 10, 2003 (FR) ...................................... 03 04444

(51) Int. Cl.

| | | |
|---|---|---|
| C08B 37/08 | (2006.01) |
| A61L 27/20 | (2006.01) |
| A61L 27/50 | (2006.01) |
| A61L 27/52 | (2006.01) |
| C08J 3/24 | (2006.01) |
| C08L 5/08 | (2006.01) |

(52) U.S. Cl.
CPC .............. *C08B 37/0072* (2013.01); *A61L 27/20* (2013.01); *A61L 27/50* (2013.01); *A61L 27/52* (2013.01); *C08J 3/24* (2013.01); *C08J 2305/08* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 2,128,827 A | 8/1938 | Killian |
| 3,548,056 A | 12/1970 | Eigen |
| 3,763,009 A | 10/1973 | Suzuki |
| 3,949,073 A | 4/1976 | Daniels |
| 4,060,081 A | 11/1977 | Yannas |
| 4,140,537 A | 2/1979 | Luck |
| 4,233,360 A | 11/1980 | Luck |
| 4,273,705 A | 6/1981 | Kato |
| 4,279,812 A | 7/1981 | Cioca |
| 4,424,208 A | 1/1984 | Wallace |
| 4,501,306 A | 2/1985 | Chu |
| 4,582,640 A | 4/1986 | Smestad |
| 4,582,865 A | 4/1986 | Balazs |
| 4,605,691 A | 8/1986 | Balazs |
| 4,636,524 A | 1/1987 | Balazs |
| 4,642,117 A | 2/1987 | Nguyen |
| 4,713,448 A | 12/1987 | Balazs |
| 4,716,154 A * | 12/1987 | Malson et al. ................... 514/54 |
| 4,772,419 A | 9/1988 | Malson et al. |
| 4,803,075 A | 2/1989 | Wallace |
| 4,886,787 A | 12/1989 | de Belder |
| 4,896,787 A | 1/1990 | Delamour |
| 5,009,013 A | 4/1991 | Wiklund |
| 5,087,446 A | 2/1992 | Suzuki |
| 5,091,171 A | 2/1992 | Yu |
| 5,143,724 A | 9/1992 | Leshchiner |
| 5,246,698 A | 9/1993 | Leshchiner |
| 5,314,874 A | 5/1994 | Miyata |
| 5,328,955 A | 7/1994 | Rhee |
| 5,356,883 A | 10/1994 | Kuo |
| 5,399,351 A | 3/1995 | Leshchiner |
| 5,428,024 A | 6/1995 | Chu |
| 5,531,716 A | 7/1996 | Luzio |
| 5,565,519 A | 10/1996 | Rhee |

(Continued)

FOREIGN PATENT DOCUMENTS

| | | |
|---|---|---|
| CA | 0949965 | 6/1974 |
| EP | 0273823 | 7/1988 |
| EP | 0416250 | 3/1991 |
| EP | 0416846 | 3/1991 |
| EP | 1247522 | 10/2002 |
| EP | 1398131 | 3/2004 |
| EP | 1419792 | 5/2004 |
| EP | 1532991 | 5/2005 |
| EP | 1726299 | 11/2006 |
| EP | 2236523 | 6/2010 |

(Continued)

OTHER PUBLICATIONS

Gomis et al. Arthritis & Rheumatism vol. 50, No. 1, Jan. 2004, pp. 314-326.*

(Continued)

*Primary Examiner* — Layla Bland
(74) *Attorney, Agent, or Firm* — Linda Allyson Nassif

(57) ABSTRACT

A process for the crosslinking of at least one polymer selected from polysaccharides and derivatives thereof, which is carried out in an aqueous solvent by the action of an effective and non-excessive amount of at least one crosslinking agent, characterized in that it is carried out on a mixture containing at least one low-molecular weight polymer and at least one high-molecular weight polymer. A process for the preparation of an injectable monophase hydrogel of at least one crosslinked polymer selected from polysaccharides and derivatives thereof. Crosslinked polymers and injectable monophase hydrogels respectively obtainable by each of said processes.

9 Claims, 1 Drawing Sheet

(56) References Cited

U.S. PATENT DOCUMENTS

| | | |
|---|---|---|
| 5,571,503 A | 11/1996 | Mausner |
| 5,614,587 A | 3/1997 | Rhee |
| 5,616,568 A | 4/1997 | Pouyani |
| 5,616,611 A | 4/1997 | Yamamoto |
| 5,616,689 A | 4/1997 | Shenoy |
| 5,633,001 A | 5/1997 | Agerup |
| 5,643,464 A | 7/1997 | Rhee |
| 5,676,964 A | 10/1997 | Della Valle |
| 5,823,671 A | 10/1998 | Mitchell |
| 5,824,333 A | 10/1998 | Scopelianos |
| 5,827,529 A | 10/1998 | Ono |
| 5,843,907 A | 12/1998 | Sakai |
| 5,880,107 A | 3/1999 | Buenter |
| 5,886,042 A | 3/1999 | Yu |
| 5,935,164 A | 8/1999 | Iverson |
| 5,980,930 A | 11/1999 | Fenton |
| 6,013,679 A | 1/2000 | Kuo |
| 6,066,325 A | 5/2000 | Wallace |
| 6,224,857 B1 | 5/2001 | Romeo |
| 6,335,035 B1 | 1/2002 | Drizen |
| 6,372,494 B1 | 4/2002 | Naughton |
| 6,383,218 B1 | 5/2002 | Sourdille |
| 6,383,219 B1 | 5/2002 | Telandro |
| 6,418,934 B1 | 7/2002 | Chin |
| 6,521,223 B1 | 2/2003 | Calias |
| 6,544,503 B1 | 4/2003 | Vanderhoff |
| 6,627,620 B1 | 9/2003 | Nielsen |
| 6,630,486 B1 | 10/2003 | Royer |
| 6,685,963 B1 | 2/2004 | Taupin |
| 6,716,251 B1 | 4/2004 | Asius |
| 6,734,298 B1 | 5/2004 | Barbucci |
| 6,767,924 B2 | 7/2004 | Yu |
| 6,767,928 B1 | 7/2004 | Murphy |
| 6,852,255 B2 | 2/2005 | Yang |
| 6,893,466 B2 | 5/2005 | Trieu |
| 6,903,199 B2 | 6/2005 | Moon |
| 6,921,819 B2 * | 7/2005 | Piron et al. .................. 536/55.3 |
| 6,924,273 B2 | 8/2005 | Pierce |
| 6,939,562 B2 | 9/2005 | Spiro |
| 6,979,440 B2 | 12/2005 | Shefer |
| 7,119,062 B1 | 10/2006 | Alvis |
| 7,166,570 B2 | 1/2007 | Hunter |
| 7,192,984 B2 | 3/2007 | Berg |
| 7,196,180 B2 | 3/2007 | Aeschlimann |
| 7,314,636 B2 | 1/2008 | Caseres |
| 7,491,709 B2 | 2/2009 | Carey |
| 7,741,476 B2 | 6/2010 | Lebreton |
| 7,902,171 B2 | 3/2011 | Reinmuller |
| 8,124,120 B2 | 2/2012 | Sadozai |
| 2002/0102311 A1 | 8/2002 | Gustavsson |
| 2002/0160109 A1 | 10/2002 | Yeo |
| 2003/0031638 A1 | 2/2003 | Joshi |
| 2003/0093157 A1 | 5/2003 | Casares |
| 2003/0119985 A1 | 6/2003 | Sehl |
| 2003/0148995 A1 | 8/2003 | Piron |
| 2004/0032056 A1 | 2/2004 | Vang |
| 2004/0101959 A1 | 5/2004 | Marko |
| 2004/0127698 A1 | 7/2004 | Tsai |
| 2004/0127699 A1 | 7/2004 | Zhao |
| 2004/0199241 A1 | 10/2004 | Gravett |
| 2004/0265389 A1 | 12/2004 | Yui |
| 2005/0101582 A1 | 5/2005 | Lyons |
| 2005/0136122 A1 | 6/2005 | Sadozai |
| 2005/0142152 A1 | 6/2005 | Leshchiner |
| 2005/0181007 A1 | 8/2005 | Hunter |
| 2005/0186261 A1 | 8/2005 | Avelar |
| 2005/0186673 A1 | 8/2005 | Geistlich |
| 2005/0227936 A1 | 10/2005 | McSwiggen |
| 2005/0271729 A1 | 12/2005 | Wang |
| 2005/0281880 A1 | 12/2005 | Wang |
| 2005/0287180 A1 | 12/2005 | Chen |
| 2006/0040894 A1 | 2/2006 | Hunter |
| 2006/0095137 A1 | 5/2006 | Chung |
| 2006/0122147 A1 | 6/2006 | Wohlrab |
| 2006/0141049 A1 | 6/2006 | Lyons |
| 2006/0147483 A1 | 7/2006 | Chaouk |
| 2006/0189516 A1 | 8/2006 | Yang |
| 2006/0194758 A1 | 8/2006 | Lebreton |
| 2006/0246137 A1 | 11/2006 | Hermitte |
| 2006/0257488 A1 | 11/2006 | Hubbard |
| 2006/0286769 A1 | 12/2006 | Tsuchiya |
| 2007/0026070 A1 | 2/2007 | Vonwiller |
| 2007/0066816 A1 | 3/2007 | Tsai |
| 2007/0077292 A1 | 4/2007 | Pinsky |
| 2007/0203095 A1 | 8/2007 | Sadozai |
| 2007/0212385 A1 | 9/2007 | David |
| 2007/0224247 A1 | 9/2007 | Chudzik |
| 2007/0298005 A1 | 12/2007 | Thibault |
| 2008/0044476 A1 | 2/2008 | Lyons |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono |
| 2008/0200430 A1 | 8/2008 | Bitterman |
| 2008/0207794 A1 | 8/2008 | Wright |
| 2008/0241252 A1 | 10/2008 | Lyons et al. |
| 2008/0268051 A1 | 10/2008 | Hughes |
| 2008/0274946 A1 | 11/2008 | Giampapa |
| 2008/0279806 A1 | 11/2008 | Cho |
| 2009/0018102 A1 | 1/2009 | Moutet |
| 2009/0022808 A1 | 1/2009 | Champion |
| 2009/0028817 A1 | 1/2009 | Niklason |
| 2009/0036403 A1 | 2/2009 | Stroumpoulis |
| 2009/0042834 A1 | 2/2009 | Karageozian |
| 2009/0093755 A1 | 4/2009 | Schroeder |
| 2009/0110671 A1 | 4/2009 | Miyata |
| 2009/0110736 A1 | 4/2009 | Boutros |
| 2009/0143331 A1 | 6/2009 | Stoumpoulis |
| 2009/0143348 A1 | 6/2009 | Tezel |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0263447 A1 | 10/2009 | Asius |
| 2009/0291986 A1 | 11/2009 | Puppas |
| 2009/0297632 A1 | 12/2009 | Waugh |
| 2010/0004198 A1 | 1/2010 | Stroumpoulis |
| 2010/0028437 A1 | 2/2010 | Lebreton |
| 2010/0035838 A1 | 2/2010 | Heber |
| 2010/0041788 A1 | 2/2010 | Voigts |
| 2010/0098764 A1 | 4/2010 | Stroumpoulis |
| 2010/0098794 A1 | 4/2010 | Armand |
| 2010/0099623 A1 | 4/2010 | Schroeder |
| 2010/0111919 A1 | 5/2010 | Abuzaina |
| 2010/0136070 A1 | 6/2010 | Dobak |
| 2010/0226988 A1 | 9/2010 | Lebreton |
| 2010/0316683 A1 | 12/2010 | Piron |
| 2011/0034684 A1 | 2/2011 | Yokokawa |

FOREIGN PATENT DOCUMENTS

| | | |
|---|---|---|
| FR | 2733427 | 10/1996 |
| FR | 2920000 | 2/2009 |
| FR | 2924615 | 6/2009 |
| JP | 55-0153711 | 11/1980 |
| JP | 2007-063177 | 3/2007 |
| WO | 86-00079 | 1/1986 |
| WO | 86-00912 | 2/1986 |
| WO | 92-00105 | 1/1992 |
| WO | 92-20349 | 11/1992 |
| WO | 96-33751 | 10/1993 |
| WO | 94-01468 | 1/1994 |
| WO | 94-02517 | 3/1994 |
| WO | 97-04012 | 6/1997 |
| WO | 98-35639 | 8/1998 |
| WO | 98-35640 | 8/1998 |
| WO | 00-01428 | 1/2000 |
| WO | 01-79342 | 10/2001 |
| WO | 02-05753 | 1/2002 |
| WO | 02-06350 | 1/2002 |
| WO | 02-09792 | 2/2002 |
| WO | 03-007782 | 1/2003 |
| WO | 02-017713 | 3/2003 |
| WO | 2004-020473 | 3/2004 |

(56) References Cited

FOREIGN PATENT DOCUMENTS

| WO | 2004-022603 | 3/2004 |
|---|---|---|
| WO | 2004-073759 | 9/2004 |
| WO | 2004-092223 | 10/2004 |
| WO | 2005-040224 | 6/2005 |
| WO | 2005-067994 | 7/2005 |
| WO | 2005-074913 | 8/2005 |
| WO | 2005-112888 | 12/2005 |
| WO | 2006-023645 | 3/2006 |
| WO | 2006-067608 | 6/2006 |
| WO | 2007-018124 | 2/2007 |
| WO | 2007-070617 | 6/2007 |
| WO | 2007-077399 | 7/2007 |
| WO | 2007-128923 | 11/2007 |
| WO | 2007-136738 | 11/2007 |
| WO | 2008-034176 | 3/2008 |
| WO | 2008-068297 | 6/2008 |
| WO | 2008-072230 | 6/2008 |
| WO | 2008-077172 | 7/2008 |
| WO | 2008-098019 | 8/2008 |
| WO | 2008-139122 | 11/2008 |
| WO | 2008-148967 | 12/2008 |
| WO | 2008-157608 | 12/2008 |
| WO | 2009-024719 | 2/2009 |
| WO | 2009-026158 | 2/2009 |
| WO | 2009-028764 | 3/2009 |
| WO | 2009-034559 | 3/2009 |
| WO | 2009-073437 | 6/2009 |
| WO | 2010-003797 | 1/2010 |
| WO | 2010-015900 | 2/2010 |
| WO | 2010-027471 | 3/2010 |
| WO | 2010-028025 | 3/2010 |
| WO | 2010-029344 | 3/2010 |
| WO | 2010-038771 | 4/2010 |
| WO | 2010-051641 | 5/2010 |
| WO | 2010-052430 | 5/2010 |
| WO | 2010-053918 | 5/2010 |
| WO | 2010-061005 | 6/2010 |

OTHER PUBLICATIONS

Adams, Mark, An Analysis of Clinical Studies of the Use of Crosslinked Hyaluronan, Hylan, in the Treatment of Osteoarthritis, The Journal of Rheumatology, 1993, 16-18, 20 (39).

Albano, Emanuele et al, Hydroxyethyl Radicals in Ethanol Hepatotoxicity, Frontiers in Bioscience, 1999, 533-540, 4.

Allemann, Inja Bogdan, Hyaluronic Acid Gel (Juvederm) Preparations in the Treatment of Facial Wrinkles and Folds, Clinical Interventions in Aging, 2008, 629-634, 3 (4).

Antunes, Alberto et al, Efficacy of Intrarectal Lidocaine Hydrochloride Gel for Pain Control in Patients Undergoing Transrectal Prostate Biopsy, Clinical Urology, 2004, 380-383, 30.

Atanassoff, Peter et al, The Effect of Intradermal Administration of Lidocaine and Morphine on the Response to Thermal Stimulation, Anesth Analg, 1997, 1340-1343, 84.

Baumann, Leslie et al, Comparison of Smooth-Gel Hyaluronic Acid Dermal Fillers with Cross-linked Bovine Collagen: A Multicenter, Double-Masked, Randomized, Within-Subject Study, Dermatologic Surgery, 2007, S128-135, 33 (2).

Beasley, Karen et al, Hyaluronic Acid Fillers: A Comprehensive Review, Facial Plastic Surgery, 2009, 86-94, 25 (2).

Beer, Kenneth, Dermal Fillers and Combinations of Fillers for Facial Rejuvenation, Dermatologic Clin, 2009, 427-432, 27 (4).

Belda, Jose et al, Hyaluronic Acid Combined With Mannitol to Improve Protection Against Free-Radical Endothelial Damage: Experimental Model, J Cataract Refract Surg, 2005, 1213-1218, 31.

Bircher, Andres et al, Delayed-type Hypersensitivity to Subcutaneous Lidocaine With Tolerance to Articaine: Confirmation by In Vivo and In Vitro Tests, Contact Dermatitis, 1996, 387-389, 34.

Bluel, K. et al, Evaluation of Reconstituted Collagen Tape as a Model for Chemically Modified Soft Tissues, Biomat. Med. Dev. Art. Org., 1981, 37-46, 9 (1).

Capozzi, Angelo et al, Distant Migration of Silicone Gel From a Ruptured Breast Implant, Silicone Gel Migration, 1978, 302-3, 62 (2).

Carlin, G. et al, Effect of Anti-Inflammatory Drugs on Xanthine Oxidase and Xanthine Oxidase Induced Depolymerization of Hyaluronic Acid, Agents and Actions, 1985, 377-384, 16 (5).

Carruthers, Jean et al, The Science and Art of Dermal Fillers for Soft-Tissue Augmentation, Journal of Drugs in Dermatology, 2009, 335-350, 8 (4).

Champion, Julie et al, Role of Target Geometry in Phagocytosis, Proc. Nat. Acad. Sci., 2006, 4930-4934, 103 (13).

Chin, Thomas et al, Allergic Hypersensitivity to Lidocaine Hydrochloride, International Society of Tropical Dermatology, 1980, 147-148.

Chvapil, Milos, Collagen Sponge: Theory and Practice of Medical Applications, Biomed Mater. Res., 1977, 721-741, 11.

Clark, D. Dick et al, The Influence of Triamcinolone Acetonide on Joint Stiffness in the Rat, The Journal of Bone and Joint Surgery, 1971, 1409-1414, 53A (7).

Cohen, Miriam et al, Organization and Adhesive Properties of the Hyaluronan Pericellular Coat of Chondrocytes and Epithelial Cells, Biophysical Journal, 2003, 1996-2005, 85.

Cui, Yu et al, The Comparison of Physicochemical Properties of Four Cross-linked Sodium Hyaluronate Gels With Different Cross-linking Agents, Advanced Materials Research, 2012, 1506-1512, 396-398.

Deland, Frank, Intrathecal Toxicity Studies with Benzyl Alcohol, Toxicology and Applied Pharmacology, 1973, 153-6, 25, Academic Press, Inc.

Dermik Laboratories, Sculptra® Aesthetic (injectable poly-L-lactic acid) Directions for Use, Product Insert, Jul. 2009, 12 Pages.

Desai, Ur et al, molecular Weight of Heparin Using 13C Nuclear Magnetic Resonance Spectroscopy, J Pharm Sci., 1995, 212-5, 84 (2).

Donald Buck, Injectable Fillers For Facial Rejuvenation: a Review, Journal of Plastic, Reconstructive & Aesthetic Surgery, 2009, 11-18, 62.

Eyre, David et al, Collagen Cross-Links, Top Curr Chem, 2005, 207-229, 247, Springer-Verlag, Berlin Heidelberg.

Falcone, Samuel et al, Crosslinked Hyaluronic Acid Dermal Fillers: A Comparison of Rheological Properties, Journal of Biomedical Materials Research, 2008, 264-271, 87 (1).

Falcone, Samuel et al, Temporary Polysaccharide Dermal Fillers: A Model for Persistence Based on Physical Properties, Dermatologic Surgery, 2009, 1238-1243, 35 (8).

Farley, Jon et al, Diluting Lidocaine and Mepivacaine in Balanced Salt Solution Reduces the Pain of Intradermal Injection, Regional Anesthesia, 1994, 48-51, 19 (1).

Frati, Elena et al, Degradation of Hyaluronic Acid by Photosensitized Riboflavin In Vitro. Modulation of the Effect by Transition Metals, Radical Quenchers, and Metal Chelators, Free Radical Biology Medicine, 1996, 1139-1144, 22 (7).

Fujinaga, Masahiko et al, Reproductive and Teratogenic Effects of Lidocaine in Sprague-Dawley Rats, Anesthesiology, 1986, 626-632, 65.

Gammaitoni, Arnold et al, Pharmacokinetics and Safety of Continuously Applied Lidocaine Patches 5%, Am J Health Syst Pharm, 2002, 2215-2220, 59.

Ginshicel MH, GinShiCel MH Hydroxy Propyl Methyl Cellulose, Retrieved on Nov. 12, 2008 http://www.ginshicel.cn/MHPC.html, 2007, p. 1-3, 2 (3).

Gold, Michael, Use of Hyaluronic Acid Fillers for the Treatment of the Aging Face, Clin. Interventions Aging, 2007, 369-376, 2 (3).

Goldberg, David, Breakthroughs in US dermal fillers for facial soft-tissue augmentation, Journal of Cosmetic and Laser Therapy, 2009, 240-247, 11, Informa UK Ltd.

Gomis, Ana et al, Effects of Different Molecular Weight Elastoviscous Hyaluronan Solutions on Articular Nociceptive Afferents, Arthritis & Rheumatism, Jan. 2004, 314-326, 50(1).

Graefe, Hendrik et al, Sensitive and Specific Photometric Determination of Mannitrol, Clin Chem Lab Med, 2003, 1049-1055, 41 (8).

Grecomoro, G. et al, Intra-articular treatment with sodium hyaluronate in gonarthrosis: a controlled clinical trial versus placebo, Pharmatherapeutica, 1987, 137-141, 5 (2).

(56) References Cited

OTHER PUBLICATIONS

Grillo, Hermes et al, Thermal Reconstitution of Collagen from Solution and the Response to Its Heterologous Implantation, JSR, 1962, 69-82, 2 (1).

Hassan, HG et al, Effects of Adjuvants to Local Anaesthetics on Their Duration. III. Experimental Studies of Hyaluronic Acid, Acta Anaesthesiol Scand., 1985, 1, 29 (4).

Hayashibara, AA2G, Sep. 23, 2007, Retrieved on Jan. 17, 2012, http://web.archive.org/web/20070923072010/http://www.hayashibara-intl.com/cosmetics/aa2g.html.

Helliwell, Philip, Use of an objective measure of articular stiffness to record changes in finger joints after intra-articular injection of corticosteroid, Annals of Rheumatic Diseases, 1997, 71-73, 56.

Hertzberger, R. et al, Intra-articular steroids in pauciarticular juvenile chronic arthritis, type 1, European Journal of Pediatrics, 1991, 170-172, 150.

Hetherington, NJ et al, Potential for Patient Harm from Intrathecal Administration of Preserved Solutions, Med J Aust., 2000, 1.

Hurst, E., Adhesive Arachnoiditis and Vascular Blockage Caused by Detergents and other Chemical Irritants: An Experimental Study, J Path. Bact., 1955, 167, 70.

Jones, Adrian et al, Intra-articular Hyaluronic Acid Compared to Intra-articular Triamcinolone Hexacetonide in Inflammatory Knee Osteoarthritis, Osteoarthritis and Cartilage, 1995, 269-273, 3.

Kablik, Jeffrey et al, Comparative Physical Properties of Hyaluronic Acid Dermal Fillers, Dermatol Surg, 2009, 302-312, 35.

Klein, A., Skin Filling Collagen and Other Injectables of the Skin, Fundamentals of Cosmetic Surgery, 2001, 491-508, 3 (19).

Kopp, Sigvard et al, The Short-term Effect of Intra-articular Injections of Sodium Hyaluronate and Corticosteroid on Temporomandibular Joint Pain and Dysfunction, Journal of Oral and Maxillofacial Surgery, 1985, 429-435, 43.

Kulicke, Werner-Michael et al, Visco-elastic Properties of Sodium Hyaluronate Solutions, American Institute of Physics, 2008, 585-587.

Laeschke, Klaus, Biocompatibility of Microparticles into Soft Tissue Fillers, Semin Cutan Med Surg, 2004, 214-217, 23.

Lamar, PD et al, Antifibrosis Effect of Novel Gels in Anterior Ciliary Slerotomy (ACS), 2002, 1 Page, The Association for Research in Vision and Ophthalmology, Inc.

Levy, Jaime et al, Lidocaine Hypersensitivity After Subconjunctival Injection, Can J Ophthalmol, 2006, 204-206, 41.

Lindvall, Sven et al, Influence of Various Compounds on the Degradation of Hyaluronic Acid by a Myeloperoxidase System, Chemico-Biological Interactions, 1994, 1-12, 90.

Lupo, Mary, Hyaluronic Acid Fillers in Facial Rejuvenation, Seminars in Cutaneous Medicine and Surgery, 2006, 122-126, 25.

Mackley, Christine et al, Delayed-Type Hypersensitivity to Lidocaine, Arch Dermatol, 2003, 343-346, 139.

Malahyde Information Systems, Intramed Mannitol 20% m/v Infusion, 2010, 2 Pages.

Mancinelli, Laviero et al, Intramuscular High-dose Triamcinolone Acetonide in the Treatment of Severe Chronic Asthma, West J Med, 1997, 322-329, 167 (5).

Matsumoto, Alan et al, Reducing the Discomfort of Lidocaine Administration Through pH Buffering, Journal of Vascular and Interventional Radiology, 1994, 171-175, 5 (1).

McCarty, Daniel et al, Inflammatory Reaction after Intrasynovial Injection of Microcrystalline Adrenocorticosteroid Esters, Arthritis and Rheumatism, 1964, 359-367, 7 (4).

McCleland, Marcee et al, Evaluation of Artecoll Polymethylmethacrylate Implant for Soft-Tissue Augmentation: Biocompatibility and Chemical Characterization, Plastic & Reconstructive Surgery, 1997, 1466-1474, 100 (6).

McPherson, John et al, Development and Biochemical Characterization of Injectable Collagen, Journal of Dermatol Surg Oncol, 1988, 13-20, 14 (Suppl 1) 7.

Miinews.com, Juvederm Raises Standards, Aesthetic Buyers Guide, 2007, 1, 4-7.

Millay, Donna et al, Vasoconstrictors in Facial Plastic Surgery, Arch Otolaryngol Head Neck Surg., 1991, 160-163, 117.

Orvisky, E. et al, High-molecular-weight Hyaluronan—a Valuable Tool in Testing the Antioxidative Activity of Amphiphilic Drugs Stobadine and Vinpocetine, Journal of Pharm. Biomed. Anal., 1997, 419-424, 16.

Osmitrol (generic name Mannitol), Official FDA Information, side effects and uses, http://www.drugs.com/pro/osmitrol.html, 2010, 10 Pages.

Park, Si-Nae et al, Biological Characterization of EDC-Crosslinked Collagen-Hyaluronic Acid Matrix in Dermal Tissue Restoration, Biomaterials, 2003, 1631-1641, 24.

Park, Si-Nae et al, Characterization of Porous Collagen/Hyaluronic Acid Scaffold Modified by 1-Ethyl-3-(3-Dimethylaminopropyl)Carbodiimide Cross-Linking, Biomaterials, 2002, 1205-1212, 23.

Powell. Michael, Stability of Lidocaine in Aqueous Solution: Effect of Temperature, pH, Buffer, and Metal Ions on Amide Hydrolysis, Pharmaceutical Research, 1987, 42-45, 4 (1).

Prestwich, Glenn, Evaluating Drug Efficacy and Toxicology in Three Dimensions: Using Synthetic Extracellular Matrices in Drug Discovery, Accounts of Chemical Research, Jan. 2008, 139-148, 41(1).

Product Info, Visiol, TRB Chemedica Ophthalmic Line, p. 1-2.

Rehakova, Milena et al., Properties of Collagen and Hyaluronic Acid Composite Materials and Their Modification by Chemical Crosslinking, Journal of Biomedical Materials Research, 1996, 369-372, 30, US.

Remington's Pharmaceutical Sciences, 1980, 16th Edition, Mack Publishing Company, Easton, Pennsylvania.

Rosenblatt, J. et al, Chain Rigidity and Diffusional Release in Biopolymer Gels, Controlled Release Society, 1993, 264-265, 20.

Rosenblatt, J. et al, The Effect of Collagen Fiber Size Distribution on the Release Rate of Proteins from Collagen Matrices by Diffusion, J Controlled release, 1989, 195-203, 9.

Sannino, A. et al, Crosslinking of Cellulose Derivatives and Hyaluronic Acid With Water-soluble Carbodiimide, Polymer, 2005, 11206-11212, 46.

Segura, Tatiana et al, Crosslinked Hyaluronic Acid Hydrogels: A Strategy to Functionalize and Pattern, Biomaterials, 2004, 359-371, 26 (4).

Selvi, Enrico et al, Arthritis Induced by Corticosteroid Crystals, The Journal of Rheumatology, 2004, 622, 31 (3).

Serban, Monica et al, Modular Extracellular Matrices: Solutions for the Puzzle, Methods, 2008, 93-98, 45 (1).

Shu, X. Zheng et al, In Situ Crosslinkable Hyaluronan Hydrogels for Tissue Engineering, Biomaterials, 2004, 1339-1348, 25.

Shu, Xiao et al, Synthesis and evaluation of injectable, in situ crosslinkable synthetic extracellular matrices for tissue engineering, Journal of Biomedical Materials Research, 2006, 902-912, 79A.

Silver, Frederick et al, Physical Properties of Hyaluronic Acid and Hydroxypropylmethylcellulose in Solution: Evaluation of Coating Ability, Journal of Applied Biomaterials, 1994, 89-98, 5.

Skardal, Aleksander et al, Bioprinting Vessel-Like Constructs Using Hyaluronan Hydrogels Crosslinked With Tetrahedral Polyethylene Glycol Tetracrylates, Biomaterials, 2010, 6173-6181, 31.

Smith, Kevin et al, Five Percent Lidocaine Cream Applied Simultaneously to the Skin and Mucosa of the Lips Creates Excellent Anesthesia for Filler Injections, Dermatol Surg, 2005, 1635-1637, 31.

Tezel, Ahmet et al, The science of hyaluronic acid dermal fillers, Journal of Cosmetic and Laser Therapy, 2008, 35-42, 10.

Visiol, Viscoelstic Gel for Use in Ocular Surgery, http://www.trbchemedica.com/index.php/option=com_content&tas, 2010, 1 Page.

Wahl, Gregor, European Evaluation of a New Hyaluronic Acid Filler Incorporating Lidocaine, Journal of Cosmetic Dermatology, 2008, 298-303, 7.

Waraszkiewicz, Sigmund et al, Stability-Indicating High-Performance Liquid Chromatographic Analysis of Lidocaine Hydrochloride and Lidocaine Hydrochloride with Epinephrine Injectable Solutions, J of Pharmaceutical Sciences, 1981, 1215-1218, 70 (11).

Weidmann, Michael, New Hyaluronic Acid Filler for Subdermal and Long-lasting Volume Restoration of the Face, European Dermatology, 2009, 65-68.

(56) References Cited

OTHER PUBLICATIONS

Xia, Yun et al, Comparison of Effects of Lidocaine Hydrochloride, Buffered Lidocaine, Diphenhydramine, and Normal Saline After Intradermal Injection, J of Clinical Anesthesia, 2002, 339-343, 14.

Yeom, Junseok et al, Effect of Cross-linking Reagents for Hyaluronic Acid Hydrogel Dermal Fillers on Tissue Augmentation and Regeneration, Bioconjugate Chemistry, 2010, 240, 21, American Chemical Society.

Yui, Nobuhiko et al, Inflammation Responsive Degradation of Crosslinked Hyaluronic Acid Gels, J of Controlled Release, 1992, 105-116, 26.

Yui, Nobuhiko et al, Photo-responsive Degradation of Heterogeneous Hydrogels Comprising Crosslinked Hyaluronic Acid and Lipid Microspheres for Temporal Drug Delivery, J of Controlled Release, 1993, 141-145, 26.

Yun, Yang H. et al., Hyaluronan Microspheres for Sustained Gene Delivery and Site-Specific Targeting, Biomaterials, 2004, 147-157, 25, US.

Zulian, F. et al, Triamcinolone Acetonide and Hexacetonide Intraarticular Treatment of Symmetrical Joints in Juvenile Idiopathic Arthritis: A Double-blind Trial, Rheumatology, 2004, 1288-1291, 43.

* cited by examiner

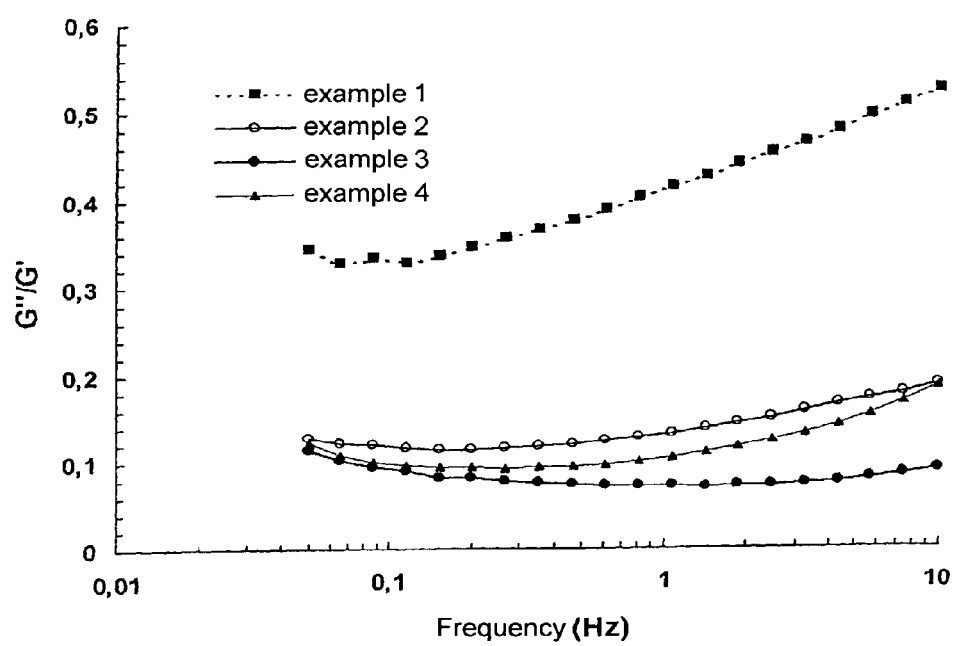

CROSS-LINKING OF LOW-MOLECULAR WEIGHT AND HIGH-MOLECULAR WEIGHT POLYSACCHARIDES, PREPARATION OF INJECTABLE MONOPHASE HYDROGELS, POLYSACCHARIDES AND HYDROGELS OBTAINED

CROSS REFERENCE TO RELATED APPLICATIONS

This application is a continuation of U.S. patent application Ser. No. 13/566,767, filed Aug. 3, 2012, which is a continuation of U.S. patent application Ser. No. 12/782,488, filed May 18, 2010, now U.S. Pat. No. 8,338,388, which is a divisional of U.S. patent application Ser. No. 10/552,309, filed Oct. 7, 2005, now U.S. Pat. No. 7,741,476, which is a U.S. National Phase Application of PCT No. PCT/FR04/00870, filed Apr. 8, 2004, which claims priority from French patent application No. 030444, filed Apr. 10, 2003, the entire disclosure of each of these applications being incorporated herein by reference.

BACKGROUND OF THE INVENTION

The present invention relates to:
a novel process for the crosslinking of at least one polymer selected from polysaccharides and derivatives thereof;
a process for the preparation of an injectable monophase hydrogel of at least one such polymer; and
the crosslinked polymers and injectable monophase hydrogels respectively obtainable by each of said processes.

DESCRIPTION OF THE RELATED ART

The hydrogels in question, based on said crosslinked polymers, have numerous outlets, especially as filling materials in plastic, cosmetic and dental surgery, in ophthalmology, in orthopedics, etc., as products for preventing tissue adhesions, in general surgery, in urology, etc. Said hydrogels are particularly suitable for repairing vocal cords. The outlets indicated above for products of this type, without implying any limitation, are familiar to those skilled in the art.

The invention is the result of a genuine effort to optimize the operation of crosslinking the polymers in question with a view to obtaining injectable monophase hydrogels that are of particular value in respect of the following compromise: on the one hand mechanical properties and remanence, and on the other hand injectability (with acceptable injection forces and injection needle diameters).

It is pointed out here that the term "injectable" employed in the present text, with reference to both the hydrogels of the prior art and the hydrogels of the invention, denotes manual injectability by means of syringes equipped with conventional needles (having a diameter of between 0.1 and 0.5 mm). Within the framework of the present invention, it is possible in particular to formulate hydrogels that can be injected through hypodermic needles of 30 G½, 27 G½, 26 G½ and 25 G.

According to the prior art, hydrogels, especially injectable hydrogels, have already been prepared from polysaccharides and derivatives thereof—especially hyaluronic acid salts—having a zero, low or high degree of crosslinking.

With reference to the specific problem of injectability, biphase compositions have been proposed whose continuous phase, in particular, is based on such hydrogels. The continuous phase serves as a plasticizer, injection vehicle for a disperse phase. This disperse phase is more or less solid and more or less differentiated from the continuous phase. Thus:

the biphase compositions described in patent application EP-A-0 466 300 consist of two bioabsorbable phases—continuous and disperse—and take the form of slurries. Said two phases are advantageously prepared from fibers of Hylan (natural hyaluronic acid chemically modified in situ in order to facilitate its extraction from the tissues);

the biphase compositions described in patent application WO-A-96 337 51 also have two bioabsorbable phases with a better separation, the disperse phase consisting of insoluble fragments of a highly crosslinked polymer hydrogel (selected from hyaluronic acid and its salts);

the biphase compositions described in patent application WO-A-00 014 28 contain a non-bioabsorbable disperse phase (particles of at least one hydrogel of a (co)polymer obtained by the polymerization and crosslinking of acrylic acid and/or methacrylic acid and/or at least one derivative of said acids) suspended in an aqueous solution of a crosslinked or non-crosslinked polymer selected from proteins, polysaccharides and derivatives thereof.

These biphase systems are not fully satisfactory insofar as they are associated with justifiable fears of uneven flow during injection and particularly after injection, a more rapid disappearance of the continuous phase (having a zero or low degree of crosslinking) and hence an at least partial loss of the desired effect, especially filling effect.

Monophase hydrogels, developed from the same types of polymers, were therefore also proposed in parallel.

In patent applications WO-A-98 356 39 and WO-A-98 356 40, the product in question is not an injectable hydrogel but a product of solid consistency. Said patent applications in fact describe ocular implants used to temporarily fill a surgically created void. The hydrogel developed in U.S. Pat. No. 4,716,154 is proposed as a substitute for the vitreous body. The polymer in question (sodium hyaluronate) has a very low degree of crosslinking in order to obtain an injectable hydrogel. The monophase hydrogel described in patent application WO-A-02 057 53 is laden with an antiseptic that is effective in protecting it from free radicals after implantation. Patent application WO-A-02 063 50 describes a process capable of generating this type of hydrogel that is very homogeneous throughout.

All these monophase hydrogels were obtained from high-molecular weight polymers crosslinked using an effective and non-excessive amount of at least one crosslinking agent, in an aqueous solvent.

SUMMARY OF THE INVENTION

In the light of this prior art, the inventors wished to improve the efficacy of crosslinking of the polymer in question, especially in order to improve the degradation resistance (remanence) of the implanted hydrogel while at the same time preserving the possibility of injecting said hydrogel under acceptable conditions.

To improve the crosslinking efficacy, the inventors initially considered using more crosslinking agent. This approach was quickly discarded on the grounds that it inescapably causes denaturation of the polymer in question and chemical contamination of the crosslinked product obtained.

Said inventors then considered increasing the concentration of polymer in the reaction mixture. In the same way, this second approach had to be discarded, a priori, because of the polymers conventionally used hitherto, namely high-molecular weight polymers. Thus sodium hyaluronate is always used with high molecular weights (Mw $10^6$ Da, $\approx 2.10^6$ Da, $3.10^6$ Da) at concentrations close to the maximum concentration, which is about 105-110 mg/g. Using it at a higher concentration is difficult (the viscosity of the reaction mixture becomes too high) and inescapably causes problems of solubility, poor homogeneity, etc.

Concentrating the reaction medium, on the other hand, is found to be possible with low-molecular weight polymers (sodium hyaluronate of molecular weight 300,000 Da, having an intrinsic viscosity of 600 ml/g (those skilled in the art are perfectly familiar with the relationship between these two parameters: molecular weight (M) and intrinsic viscosity ($\eta$), which is given by the Mark-Houwink formula: $M=k\eta^\alpha$, the values of k and $\alpha$ depending on the nature of the polymer in question), can be concentrated from 110 to 200 mg/g). Unfortunately the crosslinked polymer obtained generates an inhomogeneous, injectable biphase hydrogel under these conditions.

In such a context, the inventors surprisingly established that associating low-molecular weight polymer(s) with high-molecular weight polymer(s) affords an excellent compromise, namely the possibility of generating, for a non-excessive degree of crosslinking (equivalent to that of the prior art), an injectable monophase hydrogel which has improved mechanical and remanence properties. This low-molecular weight/high-molecular weight association makes it possible to obtain a hydrogel that more than satisfies the following specifications:
monophase;
better mechanical properties and remanence than the equivalent products of the prior art;
unaffected or even improved injectability that is still possible with conventional injection forces using conventional injection devices.

The key factor of the crosslinking process of the invention therefore lies in the concentration of the reactants (which is greater than that of the reaction mixtures of the prior art due to the use of low-molecular weight polymer(s)), although the crosslinking of said concentrated reactants is "governed" by the use of high-molecular weight polymer(s), which guarantee the homogeneity of the crosslinked product obtained and then of the hydrogel obtained.

According to its first subject, the present invention therefore relates to a process for the crosslinking of at least one polymer selected from polysaccharides and derivatives thereof, which is carried out in an aqueous solvent by the action of an effective and non-excessive amount of at least one crosslinking agent, said process being improved in that it is carried out on a mixture containing at least one low-molecular weight polymer and at least one high-molecular weight polymer.

Said mixture of course contains said low-molecular weight polymer(s) in a sufficient amount to guarantee a relatively high concentration of polymer(s) in the reaction medium, and said high-molecular weight polymer(s) in a sufficient amount to guarantee that said crosslinked polymer obtained has a homogeneous consistency.

The crosslinking process of the invention is a process for the crosslinking of polymers selected from polysaccharides and derivatives thereof. The polymer(s) in question can therefore be natural or synthetic. Examples of natural polymers are hyaluronic acid and its salts, other glycosaminoglycans such as chondroitin sulfates, keratan sulfate, heparin and heparan sulfate, alginic acid and its biologically acceptable salts, starch, amylose, dextran, xanthan, pullulan, etc. Examples of synthetic derivatives of natural polysaccharides are carboxy cellulose, carboxymethyl cellulose, alkyl celluloses such as hydroxyethyl cellulose and hydroxypropyl methyl cellulose (HPMC), oxidized starch, etc.

The process of the invention is suitable for the crosslinking of any one of these polymers insofar as said polymer is used with low and high molecular weights.

The process of the invention is suitable for the crosslinking of mixtures of such polymers, said mixtures containing at least one low-molecular weight polymer and at least one high-molecular weight polymer.

The terms "low" and "high" applied to the molecular weights in question obviously cannot be defined more precisely at this stage of the description of the invention since they depend on the mixture in question and the nature of the polymer(s) present. Likewise, it is not generally possible to indicate the relative proportions in which the polymer(s) present is(are) used. However, those skilled in the art have a perfect understanding of the spirit of the invention, which is to concentrate the reaction medium containing the low-molecular weight polymer(s), but to introduce at least one high-molecular weight polymer to moderate and control the crosslinking in question. The aim is to obtain a coherent crosslinked product that is the precursor of a monophase hydrogel. It is desirable to avoid the formation of lumps that may be coherent when crosslinking has ended, but capable of losing their coherence when the injectable hydrogel is prepared.

The above explanations are given a posteriori. The result obtained was in no way predictable.

Within the framework of one advantageous variant, the reaction medium contains a single polymer which is used with at least two differentiated molecular weights, at least one being low and at least one being high. Within the framework of this advantageous variant, the same polymer is preferably used with a single low molecular weight and a single high molecular weight.

The polymer in question is advantageously a hyaluronic acid salt. It is very advantageously selected from the sodium salt, the potassium salt and mixtures thereof. It preferably consists of the sodium salt (NaHA).

In the context of the crosslinking of this type of polymer, those skilled in the art understand that said crosslinking is carried out in a basic aqueous solvent. In general, said crosslinking is obviously carried out under pH conditions that favor the dissolution of the polymer in question.

In the context of the crosslinking of this type of polymer (hyaluronic acid salt(s)), in one preferred variant of carrying out the crosslinking, the reaction mixture contains:
at least one hyaluronic acid salt of low molecular weight m, where $M \leq 9.9 \cdot 10^5$ Da, advantageously $10^4$ Da$\leq m \leq 9.9 \cdot 10^5$ Da; and
at least one hyaluronic acid salt of high molecular weight M, where $M \geq 10^6$ Da, advantageously $10^6$ Da$\leq M \leq 10^8$ Da and very advantageously $1.1 \cdot 10^6$ Da$\leq M \leq 5 \cdot 10^6$ Da,
said low-molecular weight and high-molecular weight salts advantageously being of the same nature and very advantageously consisting of sodium hyaluronate (NaHA).

In such a context, said reaction mixture advantageously has an intrinsic viscosity of less than 1900 ml/g, i.e. $\Sigma \omega_i [\eta_i]_0 < 1900$ ml/g, where $\omega_i$ is the mass fraction of polymer fraction i, having an intrinsic viscosity $[\eta_i]_0$, in the reaction mixture. Those skilled in the art are familiar with the intrinsic viscosity parameter and are aware of the laws of additivity of said parameter.

The condition stated above makes it possible to obtain a monophase hydrogel that is optimized in respect of its remanence and injectability properties. It fixes the relative proportions of the salts of low molecular weight (m) and high molecular weight (M).

In the context referred to here (NaHA of molecular weights m and M), the reaction mixture advantageously contains more than 50% by weight, very advantageously more than 70% by weight, of at least one hyaluronic acid salt of low molecular weight m, and hence, logically, advantageously less than 50% by weight, very advantageously less than 30% by weight, of at least one hyaluronic acid salt of high molecular weight M.

In general, to obtain the expected effect, there is at least 5% by weight of at least one hyaluronic acid salt of high molecular weight M in the reaction mixture.

The crosslinking process of the invention is advantageously carried out with the sodium salt of hyaluronic acid used with one low molecular weight m and one high molecular weight M, said parameters then very advantageously being as follows: m≈3×10$^5$ Da and M≈3×10$^6$ Da.

Any agent known for crosslinking polysaccharides and derivatives thereof via its hydroxyl groups can be used as the crosslinking agent with all types of polymer, said crosslinking agent being at least bifunctional in order to ensure crosslinking, an epoxy compound or derivatives thereof being used in particular.

It is recommended to use bifunctional crosslinking agents, by themselves or in a mixture. It is particularly recommended to use epichlorohydrin, divinyl sulfone, 1,4-bis(2,3-epoxypropoxy)butane (or 1,4-bisglycidoxybutane or 1,4-butanediol diglycidyl ether (BDDE)), 1,2-bis(2,3-epoxypropoxy)ethylene, 1-(2,3-epoxypropyl)-2,3-epoxycyclohexane, and aldehydes such as formaldehyde, glutaraldehyde and crotonaldehyde, taken by themselves or in a mixture. It is very particularly recommended to use 1,4-bis(2,3-epoxypropoxy) butane (BDDE).

Those skilled in the art will know how to determine the effective and non-excessive amount of crosslinking agent(s) to use. It is recommended to use an effective and non-excessive amount such that the degree of crosslinking (τ), defined by the following ratio:

$$\tau = \frac{\text{Total number of reactive groups in said crosslinking agent}}{\text{Total number of disaccharide units in the polymer molecules}} \times 100,$$

is theoretically between 0.5 and 70%, advantageously between 4 and 50%.

The crosslinking process of the invention is novel by virtue of the forms in which the polymers in question are used. In other respects it is carried out in conventional manner with at least one crosslinking agent. It is noted that said crosslinking agent is generally reacted with the dissolved polymer(s), but reacting it with said polymer(s) during hydration, by the process described in WO-A-02 06 350, is in no way ruled out.

The crosslinked product obtained after carrying out the crosslinking process of the invention is generally formulated for generating the desired injectable monophase hydrogel. If necessary, it is neutralized beforehand. It has been seen that the hyaluronic acid salts are actually crosslinked in a basic medium. The formulation is carried out in a solution buffered to a pH compatible with the human body (since the hydrogel in question is generally intended for injection into the human body), said pH being between 6.5 and 7.5, advantageously between 7 and 7.4 and very advantageously between 7.1 and 7.3. The crosslinked polymer is in equilibrium in said solution. It also acquires an osmolarity compatible with that of the human body. Surprisingly, after this formulation step, the diluted crosslinked polymers of the invention are monophase hydrogels.

In one preferred variant of carrying out the invention, an injectable hydrogel of the invention is prepared by crosslinking a mixture of at least one polymer consisting of hyaluronic acid salt(s) (see above), neutralizing the crosslinked product obtained, and then formulating it into a solution buffered to a pH of between 7.1 and 7.3, at a concentration of between 10 and 40 mg/g, advantageously of between 20 and 30 mg/g.

The process for the preparation of the injectable monophase hydrogel from the crosslinked polymer (obtained by the crosslinking process constituting the first subject of the present invention) constitutes the second subject of the present invention.

We now come to the third and fourth subjects, which respectively consist of the crosslinked polymer obtainable after carrying out the crosslinking process (first subject), and the injectable monophase hydrogel obtainable by the formulation (second subject) of said crosslinked polymer, as stated above.

Said polymer and hydrogel advantageously contain low-molecular weight sodium hyaluronate and high-molecular weight sodium hyaluronate, the proportion of said low-molecular weight sodium hyaluronate very advantageously being more than 50% by weight.

The structure of the injectable monophase hydrogel—fourth subject of the present invention—is novel. Its consistency is resistant to degradation. This resistance of the hydrogel is far greater than that of the equivalent products of the prior art.

Those skilled in the art are aware that one of the methods of estimating the consistency of a hydrogel, especially of this type, is to measure the following parameter:

$$\tan \cdot \text{delta} = \frac{G''}{G'} = f(\text{stressing frequency}).$$

The hydrogels of the invention have the outlets indicated in the introduction of the present text. They are found to be particularly efficient for these purposes.

BRIEF DESCRIPTION OF THE DRAWINGS

In the drawing:

The FIGURE shows the curve tan·delta=f (stressing frequency) for each of the four hydrogels prepared according to Examples 1 to 4.

DETAILED DESCRIPTION OF THE PRESENTLY PREFERRED EMBODIMENTS

It is now proposed to illustrate the invention in its various features by means of the Examples below. More precisely:
  Example 1 illustrates the prior art (crosslinking of a polymer of high molecular weight);
  Example 2 illustrates the remarks made in the introduction of the present text (crosslinking of the same polymer of low molecular weight); and
  Examples 3 and 4 illustrate the invention (crosslinking of the same polymer of low and high molecular weight, used in different relative amounts).

These are preceded by a description of a few methods of measurement used to characterize the products in question.

Measurement of the Intrinsic Viscosity

The intrinsic viscosity of sodium hyaluronate (NaHA) (in ml/g) is determined according to the European Pharmacopeia for NaHA (2.2.9) using a capillary viscometer of the Ubbelohde type.

Measurement of the Ejection Force

No Specific Standard for this Test

The injectability of the gel based on NaHA is determined by measuring the force (in Newtons, N) required to eject the gel contained in a standard syringe, through a needle of 27 G½, at a rate of 12.5 mm/min. The tests were performed on a Verstatet® tensile device marketed by Mecmesin.

Measurement of the Remanence

The consistency of the gel is characterized at 25° C. by rheological measurement of the moduli of elasticity (G') and viscosity (G") as a function of the frequency (from 0.05 to 10 Hz), in the constant deformation domains, using a controlled stress rheometer (Carrimed CSL 500 from TA Instruments) and a cone-and-plate geometry of 4 cm 2°. This rheometer is checked and calibrated regularly. Degradation of the crosslinked gel results in a change in its consistency, which is measured by the increase in the parameter tangent delta (tan·delta=G"/G') as a function of time, at a frequency of 1 Hz. The gels are degraded by being heated to a temperature of 93° C. The time after which tan·delta reaches a value of 0.65 (corresponding to a degraded gel state) is measured at this temperature. A remanence index of 1 (corresponding to said time) was arbitrarily set for the gel of Example 1. The remanence index values indicated for the other gels are relative values.

Appearance of the Hydrogel Monophase

Microscopic appearance: no apparent liquid phase—fine fragmentation of the gel into facets
Macroscopic appearance: soft and free-flowing Biphase Microscopic appearance: gel fragments bathed in a low-viscosity liquid medium
Macroscopic appearance: "purée" that fragments very easily—no cohesion of the gel and no free-flowing appearance

EXAMPLE 1

High-Molecular Weight Fibers 3.5 g of sodium hyaluronate (NaHA) fibers of intrinsic viscosity 2800 ml/g and moisture content 8.7% are weighed out and 25.6 g of 0.25 N NaOH are added. Hydration of the fibers takes 2 h with regular manual homogenization using a spatula. 0.96 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6\%;[NaHA]_i=105$ mg/g

The reaction takes 2 h. The crosslinked product is neutralized to pH 7.2 in a phosphate buffer solution and then dialyzed. The concentration of the resulting hydrogel is then adjusted ([NaHA]$_f$=26 mg/g) and the hydrogel is mechanically homogenized before being packed into syringes and sterilized in an autoclave by means of moist heat.

Injection force after sterilization: 25 N
Remanence index of the hydrogel: 1.0
Monophase hydrogel

EXAMPLE 2

Low-Molecular Weight Fibers 1.56 g of sodium hyaluronate (NaHA) fibers of intrinsic viscosity 600 ml/g and moisture content 5.5% are weighed out and 7.15 g of 0.25 N NaOH are added. Hydration of the fibers takes 2 h with regular manual homogenization using a spatula. 0.31 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6.8\%;[NaHA]_i=174$ mg/g

The reaction takes 2 h. The crosslinked product is neutralized to pH 7.2 in a phosphate solution and then dialyzed. The concentration of the resulting hydrogel is then adjusted ([NaHA]$_f$=26 mg/g) and the hydrogel is mechanically homogenized before being packed into syringes and sterilized in an autoclave.

Injection force after sterilization: 24 N
Remanence index of the hydrogel: 6.0
Biphase hydrogel

EXAMPLE 3

Mixture of Fibers 0.763 g of sodium hyaluronate (NaHA) fibers of intrinsic viscosity 600 ml/g and moisture content 5.5% and 0.237 g of sodium hyaluronate fibers of intrinsic viscosity 2800 ml/g and moisture content 9.3% are weighed out. Proportions by weight in the mixture: 600/2800:77/23 (w/w).

The procedure remains identical to that of Example 2.

$R=[BDDE]_0/[NaHA]_0=7\%;[NaHA]_i=140$ mg/g; [NaHA]$_f$=26 mg/g

Injection force after sterilization: 15 N
Remanence index of the hydrogel: 3.6
Monophase hydrogel

EXAMPLE 4

Mixture of Fibers

The experiment of Example 3 is repeated, modifying the proportions by weight. Proportions by weight in the mixture: 600/2800:90/10 (w/w).

The procedure is identical to that of Example 2.

$R=[BDDE]_0/[NaHA]_0=6.5\%;[NaHA]_i=140$ mg/g; [NaHA]$_f$=26 mg/g

Injection force after sterilization: 14 N
Remanence index of the hydrogel: 7.7
Monophase hydrogel
Said Examples are summarized in the Table below.

TABLE

| n° | $\eta_{int.}$ (ml/g) % = proportion by weight in mixture | R = $m_{BDDE}/m_{NaHA}$ | $[NaHA]_0$ mg/g | $[NaHA]_f$ in final gel mg/g | Appearance* | G', G'', tan.delta (1 Hz) | $F_{ap\,ster}$ 27 G½ | Remanence index |
|---|---|---|---|---|---|---|---|---|
| 1 | (100%) 2800 | 6% | 105 | 26 | M | 143/65/0.40 | 25 | |
| 2 | (100%) 600 | 6.8% | 174 | 26 | B | 1300/100/0.08 | 24 | |
| 3 | (77%) 600 + (23%) 2800 | 7 | 140 | 26 | M | 262/27/0.10 | 15 | |
| 4 | (90%) 600 + (10%) 2800 | 6.5 | 140 | 26 | M | 571/41/0.07 | 14 | |

*M = monophase B = biphase
$[NaHA]_0$ = concentration of NaHA in the reaction medium at $t_0$
$[NaHA]_f$ = concentration of NaHA in the final hydrogel after reaction and dilution with a sufficient amount of phosphate buffer
G': modulus of elasticity of the final hydrogel (Pa · s) ⎫
G'': modulus of viscosity of the final hydrogel (Pa · s) ⎬ Carrimed CSL 500 rheometer
Tan.delta = G''/G' ⎭
$\eta_{int.}$: intrinsic viscosity of the NaHA fiber/Ubbelohde viscometer
F: ejection force of the gel in N through a 27 G½ needle/100 N dynamometer The attached Figure shows the following curve:

Tan·delta=f (stressing frequency) for each of the four hydrogels prepared according to Examples 1 to 4.

The rheological behavior of the hydrogels of the invention (Examples 3 and 4) is different from that of the hydrogel of the prior art (Example 1).

Furthermore, the hydrogels of the invention are monophase and thus very different from the hydrogel of Example 2 (biphase).

What is claimed:

1. An injectable hydrogel useful as a filling material in plastic surgery, the hydrogel made by a process comprising the steps of:
   1) forming a mixture of a first hyaluronic acid salt product having a first molecular weight and a second hyaluronic acid salt product having a second molecular weight greater than the first molecular weight, wherein the first hyaluronic acid salt product and the second hyaluronic acid salt product are two separate pre-existing products prior to the forming step, wherein the mixture contains about 90% by weight of the first hyaluronic acid salt product and about 10% by weight of the second hyaluronic acid salt product, wherein the first hyaluronic acid salt product is a sodium salt having a molecular weight of about $3 \times 10^5$ Da, and the second hyaluronic acid salt product is a sodium salt having a molecular weight of about $3 \times 10^6$ Da;
   2) cross-linking the mixture of step 1) in an aqueous solvent in the presence of an effective and non-excessive amount of at least one cross-linking agent, such that the degree of cross-linking, defined by the ratio: 100×(total number of reactive groups in said cross-linking agent/total number of disaccharide units in the first hyaluronic acid salt and second hyaluronic acid salt), is theoretically between 0.5 and 70%; and
   3) formulating the cross-linked mixture of step 2), into a solution buffered to a pH of between 6.5 and 7.5.

2. The hydrogel according to claim 1, wherein said mixture has an intrinsic viscosity of less than 1900 ml/g.

3. The hydrogel according of claim 1, wherein said cross-linking agent is selected from bifunctional crosslinking agents and mixtures thereof.

4. The hydrogel according to claim 1, wherein the degree of cross-linking is theoretically between 4 and 50%.

5. The hydrogel according to claim 1, wherein said cross-linking agent is selected from epichlorohydrin, divinyl sulfone, 1,4-bis(2,3-epoxypropoxy)butane, 1,2-bis(2,3-epoxypropoxy)ethylene, 1-(2,3-epoxypropyl)-2,3-epoxycyclohexane, aldehydes, and mixtures thereof.

6. The hydrogel according to claim 5, wherein said aldehydes are selected from formaldehyde, glutaraldehyde, crotonaldehyde, and mixtures thereof.

7. The hydrogel according to claim 1, wherein said cross-linking agent is 1,4-bis(2,3-epoxypropoxy)butane.

8. The hydrogel according to claim 1, wherein the pH is between 7 and 7.4.

9. The hydrogel according to claim 1, wherein the pH is between 7.1 and 7.3.

* * * * *

UNITED STATES PATENT AND TRADEMARK OFFICE
CERTIFICATE OF CORRECTION

| | | Page 1 of 1 |
|---|---|---|
| PATENT NO. | : 9,062,130 B2 | |
| APPLICATION NO. | : 14/024916 | |
| DATED | : June 23, 2015 | |
| INVENTOR(S) | : Pierre F. Lebreton | |

It is certified that error appears in the above-identified patent and that said Letters Patent is hereby corrected as shown below:

Title page
On the Page 3, in column 2, item (56) under "Other Publications", line 70, delete "Mannitrol," and insert -- Mannitol, --, therefor.

On the Page 4, in column 1, item (56) under "Other Publications", line 38, delete "Slerotomy" and insert -- Sclerotomy --, therefor.

On the Page 4, in column 1, item (56) under "Other Publications", line 49, delete "Malahyde" and insert -- Malahide --, therefor.

On the Page 4, in column 2, item (56) under "Other Publications", line 61, delete "Viscoelstic" and insert -- Viscoelastic --, therefor.

Specification
In column 2, line 67, delete "(Mw $10^6$ Da," and insert -- (Mw$\geq 10^6$ Da, --, therefor.

In column 4, line 51, delete "M$\leq$9.9$10^5$ Da," and insert -- m$\leq$9.9·$10^5$ Da, --, therefor.

Claims
In column 10, line 29, in claim 3, delete "of" and insert -- to --, therefor.

Signed and Sealed this
First Day of December, 2015

Michelle K. Lee
*Director of the United States Patent and Trademark Office*